United States Patent
Thornton et al.

(10) Patent No.: US 10,016,147 B2
(45) Date of Patent: Jul. 10, 2018

(54) METHOD AND SYSTEM FOR ESTIMATING THE SPECIFIC ABSORPTION RATE OF A TISSUE REGION PRIOR TO A MAGNETIC RESONANCE IMAGING SCAN

(71) Applicants: Michael Thornton, London (CA); Paul Picot, London (CA); Brian Rutt, Stanford, CA (US); Simone Winkler, Daly City, CA (US)

(72) Inventors: Michael Thornton, London (CA); Paul Picot, London (CA); Brian Rutt, Stanford, CA (US); Simone Winkler, Daly City, CA (US)

( * ) Notice: Subject to any disclaimer, the term of this patent is extended or adjusted under 35 U.S.C. 154(b) by 115 days.

(21) Appl. No.: 14/704,369

(22) Filed: May 5, 2015

(65) Prior Publication Data
US 2015/0316626 A1    Nov. 5, 2015

Related U.S. Application Data

(60) Provisional application No. 61/988,844, filed on May 5, 2014.

(51) Int. Cl.
*G01N 33/48* (2006.01)
*A61B 5/055* (2006.01)
*G01R 33/58* (2006.01)
*G01R 33/54* (2006.01)
*G01R 33/28* (2006.01)
*A61B 5/00* (2006.01)
*G06G 7/58* (2006.01)

(52) U.S. Cl.
CPC .......... *A61B 5/055* (2013.01); *A61B 5/7225* (2013.01); *G01R 33/288* (2013.01); *G01R 33/54* (2013.01); *G01R 33/58* (2013.01)

(58) Field of Classification Search
None
See application file for complete search history.

*Primary Examiner* — Eric S Dejong
(74) *Attorney, Agent, or Firm* — Tarolli, Sundheim, Covell & Tummino LLP

(57) ABSTRACT

A method and system for estimating a specific absorption rate of a tissue region prior to performing a magnetic resonance (MR) imaging scan on the tissue region. The method comprises radiating the tissue region with a plurality of short pulses, wherein the tissue region emits thermoacoustic signals responsive to the short pulses, receiving the thermoacoustic signals by at least one ultrasonic transducer, calculating a temperature rise of the tissue region based on the received thermoacoustic signals, scaling the temperature rise to estimate a temperature rise of the tissue region resulting from an MR imaging scan, and estimating the specific absorption rate of the tissue region based on the estimated temperature rise.

14 Claims, 4 Drawing Sheets

METHOD AND SYSTEM FOR ESTIMATING THE SPECIFIC ABSORPTION RATE OF A TISSUE REGION PRIOR TO A MAGNETIC RESONANCE IMAGING SCAN

CROSS-REFERENCE TO RELATED APPLICATIONS

This application claims the benefit of U.S. Provisional Patent Application No. 61/988,844 to Thornton at al., filed on May 5, 2014, the content of which is incorporated herein by reference in its entirety.

FIELD

This application relates to a method and system for estimating the specific absorption rate of a tissue region prior to a magnetic resonance imaging scan.

BACKGROUND

Safety is one of the most important factors in the design and use of the radiofrequency (RF) components of magnetic resonance (MR) imaging scanners. Application of high RF power levels for extended times causes a risk of patient injury due to increase in temperature of the targeted tissue region. One parameter used to characterize MR imaging safety for RF coils is the specific absorption rate (SAR). The SAR is a measure of the power absorbed per mass of tissue and is usually expressed in units of watts per kilogram (W/kg).

One method to determine the SIR involves calculating the overall average, or global, SAR. The global SAR is a measure of the average power absorbed per unit mass of tissue that is delivered to the entire mass for the body part under investigation in the patient.

Determining the SIR has become increasingly important in view of the increasing field strengths that are being utilized for MR imaging. These increasing field strengths improve image signal-to-noise ratio and contrast but result in higher SAR values and higher spatial variation of local SAR.

Some MR imaging scanners utilize parallel transmit technology, in which multiple channels are controlled independently. While parallel transmit technology helps to mitigate some of the aforementioned problems, an unconstrained combination of the power output to multiple channels can cause strong local heating effects due to possible constructive interference. As will be appreciated, this leads to high local SAR.

Various methods have been proposed to monitor the spatially varying SAR pattern to promote MR imaging safety. One method requires the measurement of spatial temperature variation within the body of a patient. The downside of this method is that temperature and SIR patterns are not identical to each other, mainly due to the effects of heat conduction and blood perfusion, which act to smooth and otherwise alter the SAR patterns. Additionally, MR imaging thermometry has a temperature resolution of approximately 1 degree Celcius. Given that the upper limit value of temperature rise in terms of safety is set to 1 degree Celcius as specified in IEC standards (IEC 60601-2-33: Particular requirements for the safety of magnetic resonance equipment for medical diagnosis), the use of MR imaging thermometry to monitor safety in MR imaging is not practical.

U.S. Patent Application Publication No 2010/0076298 to Gross discloses a method to determine the spatial distribution of the specific absorption rate in tissue that represents a measure of the absorption of electromagnetic fields emitted by means of a radiation generating element, wherein at least one item of measurement information acquired by a thermoacoustic computed tomography device is used to determine the specific absorption rate.

As be appreciated, improvements in estimating SAR are desired, it is therefore an object to provide a novel method and system for estimating the specific absorption rate of a tissue region prior to a MR imaging scan.

SUMMARY

Accordingly, in one aspect there is provided a method for estimating a specific absorption rate of a tissue region prior to performing a magnetic resonance (MR) imaging scan on the tissue region, the method comprising radiating the tissue region with a plurality of short pulses, wherein the tissue region emits thermoacoustic signals responsive to the short pulses, receiving the thermoacoustic signals by at least one ultrasonic transducer, calculating, a temperature rise of the tissue region based on the received thermoacoustic signals, scaling the temperature rise to estimate a temperature rise of the tissue region resulting from an MR imaging scan, and estimating the specific absorption rate of the tissue region based on the estimated temperature rise.

In embodiments, the short pulses are one of microwave and radio frequency pulses. The short pulses are generated by a radio frequency coil of a magnetic resonance imaging scanner. The short pulses are in increments of approximately 1 μs.

In embodiments, the method further comprises adjusting one or more parameters of a magnetic resonance imaging scanner based on the estimated specific absorption rate.

In embodiments, the tissue region is one of a brain, a heart and lungs.

According to another aspect there is provided a system for determining a specific absorption rate of to tissue region, the system comprising a radiation source configured to radiate the tissue region with a plurality of pulses, wherein the tissue region emits thermoacoustic signals responsive to the pulses, at least one ultrasonic transducer configured to receive the thermoacoustic signals, and one or more processors configured to calculate a temperature rise of the tissue region based on the plurality of received thermoacoustic signals, scale the temperature rise to estimate a temperature rise of the tissue region resulting from an MR imaging scan, and estimate the specific absorption rate of the tissue region based on the estimated temperature rise.

In embodiments, the radiation source is configured to radiate the tissue region with one of microwave and radio frequency pulses. The radiation source is configured to radiate the tissue with short pulses in increments of approximately 1 μs.

In embodiments, the radiation source and the at least one ultrasonic transducer are made of non-magnetic materials.

In embodiments, the system comprises a magnetic resonance imaging scanner, wherein one or more parameters of the magnetic resonance imaging scanner are adjusted based on the estimated specific absorption rate prior to conducting a magnetic resonance imaging scan. The radiation source is a radio frequency coil of the magnetic resonance imaging scanner.

According to another aspect there is provided a non-transitory computer-readable medium having stored thereon a computer program comprising computer program code, the computer program code executable by one or more processors to perform a method comprising calculating a temperature rise of a tissue region based on received thermoacoustic signals, scaling the temperature rise to estimate a temperature rise of the tissue region resulting from an MR imaging scan, and estimating a specific absorption rate of the tissue region based on the estimated temperature rise.

According to another aspect there is provided a method for calibrating a magnetic resonance (MR) imaging scanner, comprising calculating a temperature rise of a tissue region based on a plurality of received the signals emitted by the tissue region in response to the tissue region being radiated by a plurality of short radio frequency (RF) pulses, scaling the temperature rise to estimate a temperature rise of the tissue region resulting from an MR imaging scan, estimating the specific absorption rate of the tissue region based on the estimated temperature rise, and if the specific absorption rate is outside of a defined range, adjusting at least one parameter of the MR imaging scanner.

According to yet another embodiment there is provided a method for generating a prediction algorithm to estimate the specific absorption rate a tissue region, the method comprising (a) constructing a physical phantom representing characteristics of the tissue region, (b) generating a numeral model of the physical phantom, (c) calculating a prediction algorithm of the specific absorption rate of the physical phantom and estimating the specific absorption rate of the physical phantom using the prediction algorithm, (d) radiating the physical phantom with a plurality of radio frequency (RF) pulses and directly measuring the specific absorption rate of the physical phantom, (e) comparing the estimated specific absorption rate to the directly measured specific absorption rate, (f) if the estimation of the specific absorption rate is not accurate, updating the prediction algorithm using the directly measured specific absorption rate and repeating steps (d) and (e), and (g) if the estimation of the specific absorption rate is accurate, storing the prediction algorithm in a database.

According to still yet another embodiment there is provided a method for estimating a specific absorption rate of a tissue region prior to performing a magnetic resonance (MR) imaging scan on the tissue region, the method comprising determining one or more characteristics of the tissue region, selecting a specific absorption rate prediction algorithm based on the determined one or more characteristics from a database of validated specific absorption rate prediction algorithms, and estimating the specific absorption rate of the tissue region using the selected specific absorption rate prediction algorithm.

According to yet another embodiment there is provided a method for calibrating a magnetic resonance (MR) imaging scanner, comprising determining one or more characteristics of the tissue region, selecting a specific absorption rate prediction algorithm based on the determined one or more characteristics from a database of validated specific absorption rate prediction algorithms, estimating the specific absorption rate of the tissue region using the selected specific absorption rate prediction algorithm, and if the estimated specific absorption rate is outside of a defined range, adjusting at least one parameter of the MR imaging scanner.

BRIEF DESCRIPTION OF THE DRAWINGS

Embodiments will now be described more fully with reference to the accompanying drawings in which.

DETAILED DESCRIPTION OF EMBODIMENTS

Figure 1:
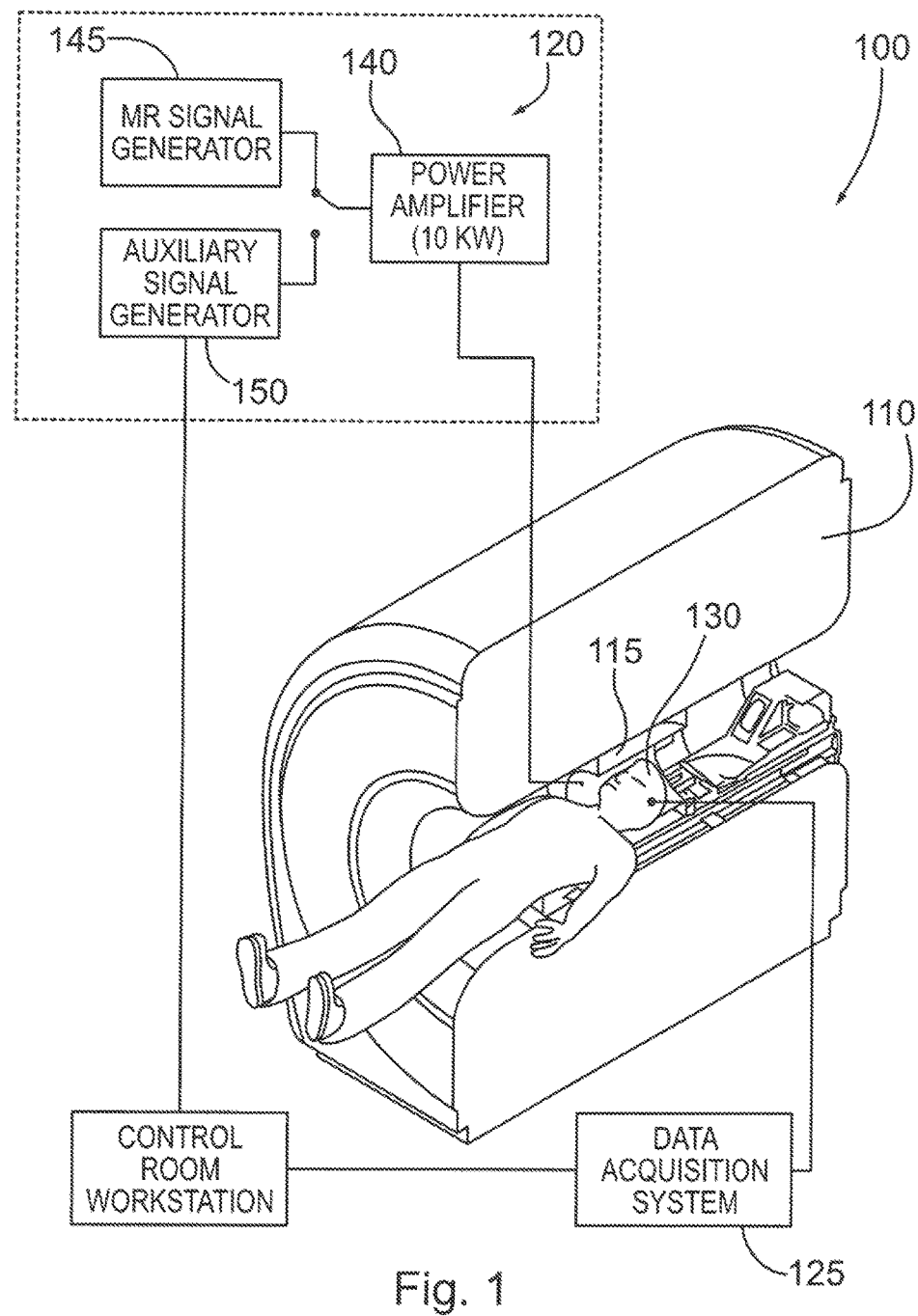
FIG. 1 is a perspective view of a system for estimating the specific absorption rate of a tissue region prior to conducting an MR imaging scan.

Turning now to FIG. 1, a system for estimating the specific absorption rate of a tissue region prior to conducting an MR imaging scan is shown and is generally identified by reference numeral 100. As can be seen, the system 100 comprises an MR imaging scanner 110 having at least one radio frequency (RF) coil 115. The at least one RF coil 115 is coupled to a power amplifier circuit 120. The power amplifier circuit 120 is coupled to a data acquisition system 125. At least one ultrasonic transducer 130 is coupled to the data acquisition system 125. The at least one ultrasonic transducer 130 is positioned within a bore of the MR imaging scanner 110. The system 100 is used to estimate the specific absorption rate (SAR of a tissue region during a pre-scan to set MR imagine parameters for an MR imaging scan.

The MR imaging scanner 110 in this embodiment is a bore-type MR imaging scanner. The general operation of the MR imaging scanner 110 will be described for ease of understanding. During imaging, a patient is positioned with the bore of the MR imaging scanner 110 and is subject to a uniform static polarizing magnetic field $B_0$ produced by a polarizing electromagnet. RF pulses are then generated by the at least one RF coil 115 in a particular sequence and are used to scan a tissue region of the patient. MR imaging signals radiated by excited nuclei in the tissue region in the intervals between consecutive RF pulses are sensed by the at feast one RF coil 115. During this MR imaging signal sensing, the polarizing magnetic field is altered by gradient coils in response to received output gradient data thereby to position encode acquired MR imaging signals.

In this embodiment, the at least one RF coil 115 is a head coil operating at 7T and the at least one RF coil 115 is used for both the estimation of SAR and the MR imaging scan. The loaded Q-factor of the at least one RF coil 115 is approximately 30 to ensure accurate rise times are used. As will be appreciated, the matching and tuning circuitry (not shown) can be adjusted to meet the desired Q-factor requirement while maintaining the required transmission efficiency required for a quality MR imaging scan. The at least one RF coil 115 is configured to emit RF pulses in response to pulse sequence data received from the data acquisition system 125 via the power amplifier circuit 120. The pulse sequence data determines the timing, strength and shape of the RF pulses in the pulse sequence. The RF sequence data is generated by the data acquisition system 125.

The power amplifier circuit 120 comprises a power amplifier 140 selectively coupled to either an MR imaging signal generator 145 or to an auxiliary signal generator 150. The two quantities relevant for ultrasonic detection sensitivity are the pulse energy required for heating a tissue region and the pulse rise time (the d(T)/dt excitation term). The MR imaging signal generator 145 delivers a peak power of 8 kW at 298 Mhz, which in a non-attenuated thermoacoustic experiment yields an ultrasound pressure of approximately 1 Pa. The power amplifier circuit 120 is configured to generate modulated pulses during the pre-scan. In this embodiment, the power amplifier circuit 120 is configured to generate a short pulse RF waveform in increments of 1 μs during the pre-scan.

The data acquisition system 125 in this embodiment is a general purpose computing device such as for example a personal computer or other suitable processing device comprising a processing structure such as for example a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computing device components to the processing unit. The general purpose computing device 125 may also comprise networking capability using Ethernet, WiFi, and/or other network format.

The data acquisition system 125 may also comprise program modules including routines, object components, data structures, and the like, and may be embodied as computer program code stored on a non-transitory computer readable medium. The non transitory computer readable medium is any data storage device that can store data. Examples of non-transitory computer readable media include for example read-only memory, random-access memory. CD-ROMs, magnetic tape, USB Keys, flash drives and optical data storage devices.

The data acquisition system 125 is configured to control RF triggering and ultrasonic data collection. A software tool is used by the data acquisition system 125 to overlay a generated SAR map onto a generated anatomic image. The data acquisition system 125 is coupled to the power amplifier circuit 120 and the at least one ultrasonic transducer 130 using data acquisition boards as is well known.

In this embodiment the at least one ultrasonic transducer 130 is a listen-only transducer and may be a PVdF transducer or a capacitive micromachined ultrasonic transducer (CMUT). The at least one ultrasound transducer 130 is non-magnetic and electrostatically shielded.

Figure 2:
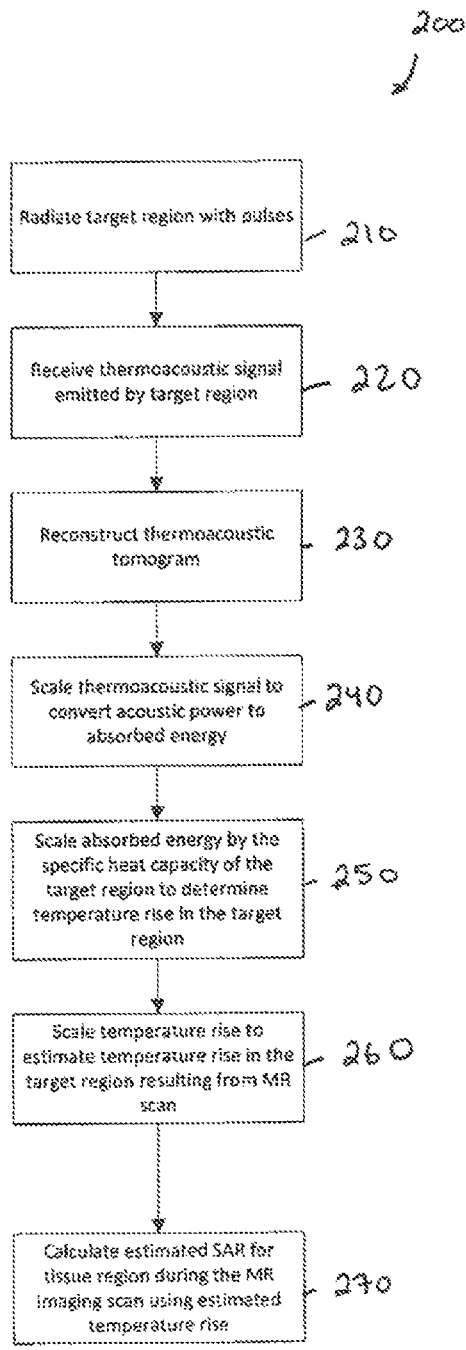
FIG. 2 is a flowchart showing a method of estimating the specific absorption rate of a tissue region prior to conducting an MR imaging scan.

Turning now to FIG. 2, a method for estimating the SAR of a tissue region poor to an MR imaging scan is shown and is generally identified by reference numeral 200. During the method, the at least one RF coil 115 is conditioned to emit short pulse RF signals into the target subject at a particular tissue region (step 210). The tissue region absorbs the RF signals and in response emits thermoacoustic signals. The thermoacoustic signals are received by the at least one transducer 130 (step 220). Using the data acquisition system 125, a thermoacoustic tomogram is reconstructed using the received thermoacoustic signals (step 230). The thermoacoustic signals are scaled by the Grunheisen coefficient to convert acoustic power to absorbed energy (step 240). The absorbed energy is scaled by the specific heat capacity of the tissue region to calculate the temperature rise in the tissue region (step 250). The calculated temperature rise in the tissue region is scaled by a ratio of the energy deposited by an RF pulse sequence of the MR imaging scan to the energy of the thermoacoustic induced RF pulsed sequence to estimate the temperature rise in the tissue region during the MR imaging scan (step 260). The estimated SAR for the tissue region during the MR imaging scan is then calculated using the estimated temperature rise (step 270).

The estimated SAR for the tissue region during the MR imaging scan may be used to calibrate or adjust one or more parameters of the MR imaging scanner to ensure patient safety.

Although step 230 is described as reconstructing a thermoacoustic tomogram, those skilled in the art will appreciate that in another embodiment focused transducers may be used to form an A-line of the received thermoacoustic signals.

System 100 and method 200 may be used to estimate the SAR for various tissue regions such as for example a patient's brain, heart or lungs. In an embodiment wherein the tissue region is the brain, two ultrasonic transducers 130 are used in this embodiment, the ultrasonic transducers 130 are positioned at respective lateral acoustic windows on the skull.

In another embodiment the SAR of a tissue region may be estimated prior to a MR imaging scan by using numerical models and algorithms. Generally, physical phantoms are constructed with known physical properties (geometric, electric, RF absorption, etc.). Using the known material properties, the SAR of the physical phantoms are estimated given thermoacoustic excitation pulses using a prediction algorithm. Thermoacoustic imaging is then used and the SAR of the physical phantom is directly measured. The estimated SAR and the directly measured SAR are compared and the prediction algorithm is updated as required. This process is repeated until the prediction algorithm is accurate. A variety of physical and numerical phantoms are constructed spanning the ranges of anticipated body sizes and other characteristics, and the direct measurement, numerical prediction and refining are repeated until a SAR prediction model comprising a number of validated SAR prediction algorithms is generated.

The number of phantoms required to generate a SAR prediction model is variable depending on the number of characteristics to model and the precision required. A design of experiments (DOE) process is used to minimize the number of phantoms required and the associated time and expense by sampling the range of required characteristics.

As will be appreciated, the combination of numerical modeling, physical model verification and DOE helps to reduce the number of phantoms required, compared to exhaustively testing every potential variation of body characteristic. Once the SAR prediction model is generated, no further validation is required until a change is made to the MR imaging scan parameters.

Figure 3:
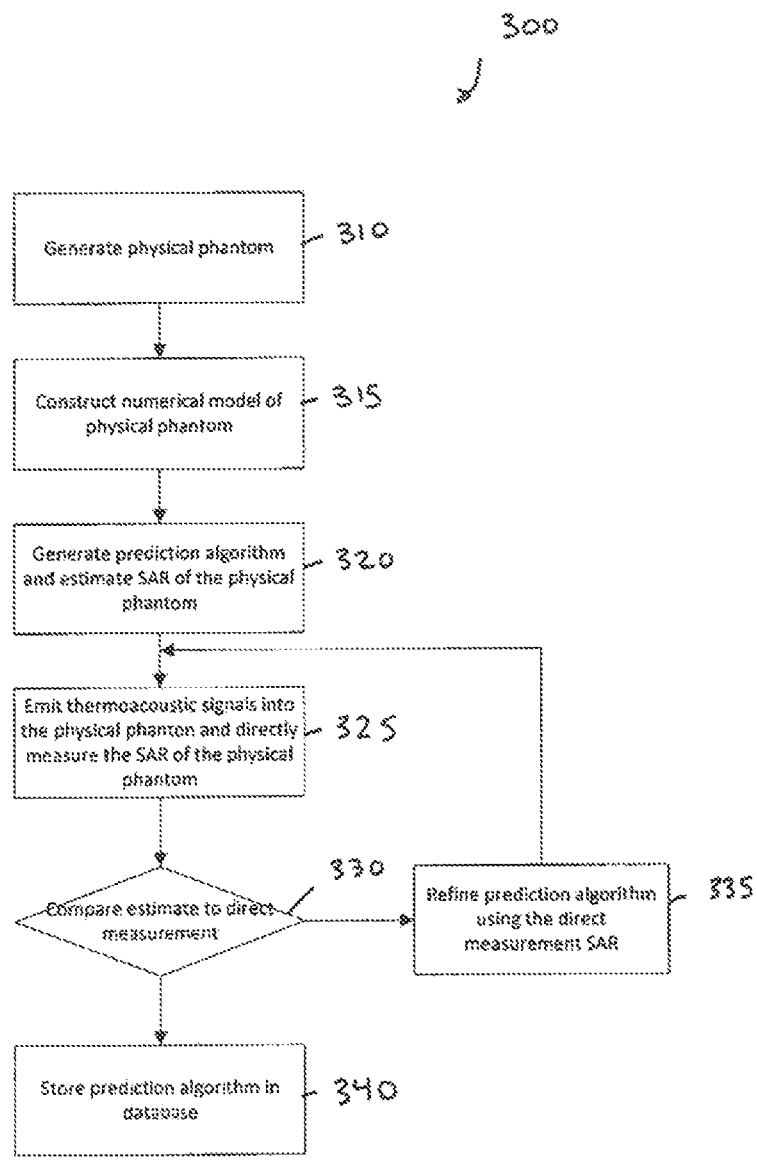
FIG. 3 is a flowchart showing a method of validating and refining numerical models and algorithms to estimate the SAR of a tissue region.
Figure 4:
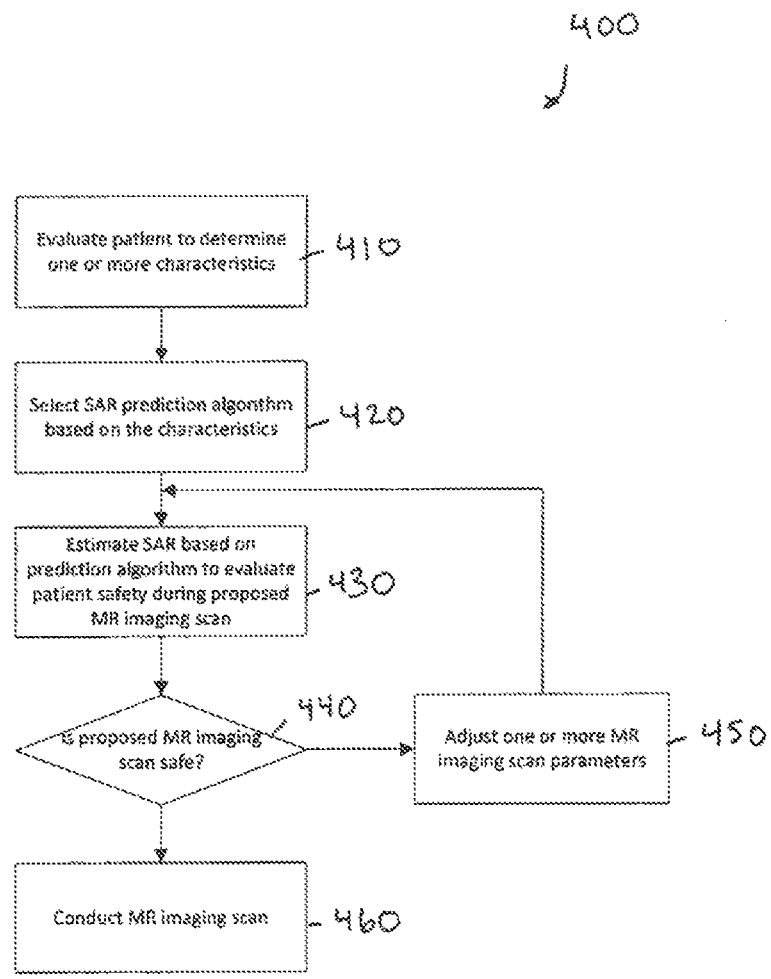
FIG. 4 is a flowchart showing a method of estimating the SAR of a tissue region using validated SAR prediction algorithms generated using the method of FIG. 3.

An exemplary method of validating and refining a prediction algorithm to estimate the SAR of a tissue region is shown in FIG. 3 and is generally identified by reference numeral 300. During the method, a physical phantom having known properties representing human anatomy such as for example a human head is constructed (step 310). The physical phantom has material properties of permittivity and conductivity similar to those of human tissue. A numerical model is constructed that represents the physical phantom including parameters such as geometry, boundary conditions and material properties (step 315). A prediction algorithm to estimate the SAR that will occur in the phantom upon stimulation of a given RF field is generated (step 320). Thermoacoustic signals are emitted into the physical phantom and the SAR of the phantom is directly measured (step 323). The direct measurement of the SAR is compared to the estimated SAR and a check is performed to determine if the prediction algorithm is validated, that is, if the estimated SAR is within a predefined threshold of the direct measurement SAR (step 330). If the comparison between the estimated SAR and the direct measurement of the SAR is not within the predefined threshold, the prediction algorithm is deemed not to be accurate The prediction algorithm is then iterated and refined based on the direct measurement of the SAR (step 335) and the method returns to step 325. This process is repeated until the comparison between the estimated SAR and the direct measurement of the SAR is within the predefined threshold. Once the prediction algorithm is validated, the prediction algorithm is stored in a database for future use (step 340). Steps 310 to 340 are repeated for various body types, organs, tissues and anatomical regions to generate a plurality of validated SAR prediction algorithms. As a result, a SAR prediction model comprising a set of validated SAR prediction algorithms is generated and stored for future use.

The SAR prediction algorithms are used to estimate the SAR of a tissue region prior to an MR imaging scan. Generally, when a patient arrives for an MR imaging scan, the patient is evaluated to define the prescription of diagnostic scans. During this process, data is gathered to measure the body characteristics, including but not limited to geometry, position and coil loading. An SAR prediction algorithm is selected based on the measured body characteristics.

An exemplary method for estimating the SAR of a tissue region using the SAR prediction model prior to an MR imaging scan is shown and is generally identified by reference numeral 400. During the method, the patient is evaluated to determine one or more characteristics such as for example body type, gender, height, weight, age (step 410). One of the SAR prediction algorithms from the SAR prediction model is selected based on the determined characteristics, that is, the SAR prediction algorithm that most closely resembles the determined characteristics of the patient (step 420). The SAR is estimated using the SAR prediction algorithm to evaluate patient safety during the proposed MP imaging scan (step 430). A check is performed to determine if the estimated SAR is within an acceptable range (step 440). If the estimated SAR is not within an acceptable range, one or more MR imaging scan parameters are adjusted (stop 450) and the method returns to step 430 to estimate the SAR during the adjusted MR imaging scan. If at step 430 the SAR is within an acceptable range, the proposed MR imaging scan is performed (step 460).

Further examples and embodiments are described in Appendices 1 and 2.

Although in embodiments above the short pulses are described as being radio frequency pulses, those skilled in the art will appreciate that the short pulses may be microwave pulses.

Those skilled in the art will appreciate that various components of the above described systems may be positioned inside or outside of a magnetic resonance imaging scanner.

Although embodiments have been described above with reference to the accompanying drawings, those of skill in the art will appreciate that variations and modifications may be made without departing from the scope thereof as defined by the appended claims.

What is claimed is:

1. A method for configuring a magnetic resonance imaging scanner based on an estimated specific absorption rate of a tissue region, the method comprising:
   radiating a tissue region with a plurality of short pulses, wherein the tissue region emits thermoacoustic signals responsive to the short pulses;
   receiving the thermoacoustic signals by at least one ultrasonic transducer;
   calculating a temperature rise of the tissue region based on the received thermoacoustic signals;
   scaling the calculated temperature rise to estimate a temperature rise of the tissue region that would occur in the event of a magnetic resonance imaging scan of the tissue region performed by a magnetic resonance imaging scanner using a current radio frequency pulse sequence;
   estimating the specific absorption rate of the tissue region based on the estimated temperature rise; and
   if the estimated specific absorption rate is outside of a defined range, configuring the magnetic resonance imaging scanner by adjusting at least one parameter of the radio frequency pulse sequence to allow the magnetic resonance imaging scanner to perform the magnetic resonance imaging scan on the tissue region while maintaining the specific absorption rate of the tissue region within the defined range.

2. The method of claim 1 wherein the short pulses are one of microwave and radio frequency pulses.

3. The method of claim 1 wherein the short pulses are generated by a radio frequency coil of the magnetic resonance imaging scanner.

4. The method of claim 1 wherein the short pulses are in increments of approximately 1 µs.

5. The method of claim 1 wherein the tissue region is one of a brain, a heart and lungs.

6. A system for configuring a magnetic resonance imaging scanner based on an estimated specific absorption rate of a tissue region comprising:
   a radiation source configured to radiate a tissue region with a plurality of pulses, wherein the tissue region emits thermoacoustic signals responsive to the pulses;
   at least one ultrasonic transducer configured to receive the thermoacoustic signals; and
   one or more processors configured to calculate a temperature rise of the tissue region based on the plurality of received thermoacoustic signals, scale the calculated temperature rise to estimate a temperature rise of the tissue region that would occur in the event of a magnetic resonance imaging scan of the tissue region performed by a magnetic resonance imaging scanner using a current radio frequency pulse sequence, estimate the specific absorption rate of the tissue region based on the estimated temperature rise, and if the estimated specific absorption rate is outside of a defined range, configuring the magnetic resonance imaging scanner by adjusting at least one parameter of the radio frequency pulse sequence to allow the magnetic resonance imaging scanner to perform the magnetic resonance imaging scan on the tissue region while maintaining the specific absorption rate of the tissue region within the defined range.

7. The system of claim 6 wherein the radiation source is configured to radiate the tissue region with one of microwave and radio frequency pulses.

8. The system of claim 7 wherein the radiation source is configured to radiate the tissue with short pulses in increments of approximately 1 µs.

9. The system of claim 6 wherein the radiation source and the at least one ultrasonic transducer are made of non-magnetic materials.

10. The system of claim 6 wherein the radiation source is a radio frequency coil of the magnetic resonance imaging scanner.

11. A non-transitory computer-readable medium having stored thereon a computer program comprising computer program code, the computer program code executable by one or more processors to perform a method of configuring a magnetic resonance imaging scanner based on an estimated specific absorption rate of a tissue region comprising:
calculating a temperature rise of a tissue region based on received thermoacoustic signals;
scaling the calculated temperature rise to estimate a temperature rise of the tissue region that would occur in the event of a magnetic resonance imaging scan of the tissue region performed by a magnetic resonance imaging scanner using a current radio frequency pulse sequence;
estimating the specific absorption rate of the tissue region based on the estimated temperature rise; and
if the estimated specific absorption rate is outside of a defined range, configuring the magnetic resonance imaging scanner by adjusting at least one parameter of the radio frequency pulse sequence to allow the magnetic resonance imaging scanner to perform the magnetic resonance imaging scan on the tissue region while maintaining the specific absorption rate of the tissue region within the defined range.

12. A method for configuring a magnetic resonance imaging scanner based on an estimated specific absorption rate of a tissue region, the method comprising:
determining one or more characteristics of a tissue region;
selecting a specific absorption rate prediction algorithm based on the determined one or more characteristics of the tissue region from a database of validated specific absorption rate prediction algorithms;
using the selected specific absorption rate prediction algorithm, estimating the specific absorption rate of the tissue region that would occur in the event of a magnetic resonance imaging scan of the tissue region performed by a magnetic resonance imaging scanner using a current radio frequency pulse sequence; and
if the estimated specific absorption rate is outside of a defined range, configuring the magnetic resonance imaging scanner by adjusting at least one parameter of the radio frequency pulse sequence to allow the magnetic resonance imaging scanner to perform a magnetic resonance imaging scan on the tissue region while maintaining the specific absorption rate of the tissue region within the defined range.

13. The method of claim 12 further comprising:
determining one or more characteristics of a patient; and
selecting the specific absorption rate prediction algorithm based on the determined one or more characteristics of the patient and the tissue region.

14. The method of claim 13 wherein the one or more characteristics of the patient are at least one of body type, gender, height, weight and age.

* * * * *